(12) United States Patent
Druzgala et al.

(10) Patent No.: US 6,387,914 B2
(45) Date of Patent: May 14, 2002

(54) ULTRASHORT ACTING HYPNOTIC BARBITURATES

(75) Inventors: Pascal Druzgala, Santa Rosa; Peter G. Milner, Los Altos Hills, both of CA (US)

(73) Assignee: ARYx Therapeutics, Sunnyvale, CA (US)

( * ) Notice: Subject to any disclaimer, the term of this patent is extended or adjusted under 35 U.S.C. 154(b) by 0 days.

(21) Appl. No.: 09/841,738

(22) Filed: Apr. 24, 2001

Related U.S. Application Data

(60) Provisional application No. 60/199,144, filed on Apr. 24, 2000.

(51) Int. Cl.[7] .................... C07D 239/62; C07D 239/42; A61K 31/505; A61K 31/515
(52) U.S. Cl. ....................... 514/270; 544/302; 544/320; 544/321; 514/272
(58) Field of Search ................................. 514/270, 272; 544/302, 320, 321

(56) References Cited

PUBLICATIONS

Porter R.J., Meldrum, B.S.[1992] "Antiepileptic drugs" Basic & Clinical Pharmacology, Katzung B.G., Ed., Appleton & Lange, Norwalk, Conn., 5th Edition, pp. 331–349.
Trevor, A.J., Way, W.L. [1992] "Sedative–hypnotics" Basic & Clinical Pharmacology, Katzhung, B.G., Ed., Appleton & Lange, Norwalk, Conn., 5th Edition, pp. 306–319.

*Primary Examiner*—John M. Ford
(74) *Attorney, Agent, or Firm*—Saliwanchik, Lloyd & Saliwanchik

(57) ABSTRACT

The subject invention concerns novel compounds that are useful as ultrashort acting hypnotic barbiturates. Specifically exemplified are derivatives of barbituric and thiobarbituric acids. They are rapidly metabolized by blood and tissue enzymes to form polar metabolites with no hypnotic activity and which are rapidly eliminated.

38 Claims, 3 Drawing Sheets

ULTRASHORT ACTING HYPNOTIC BARBITURATES

CROSS-REFERENCE TO RELATED APPLICATION

This application claims the benefit of U.S. Provisional Application No. 60/199,144, filed Apr. 24, 2000.

BACKGROUND OF THE INVENTION

The principal use of a sedative-hypnotic drug is to produce drowsiness and to promote sleep. Since sedative-hypnotic drugs usually have the capacity of producing widespread depression of the CNS, these drugs are employed for various reasons, including as antiepileptic, muscle relaxants, antianxiety drugs, and even to produce amnesia or general anesthesia. Throughout the world, more prescriptions are written for sedative-hypnotic-antianxiety drugs than for any other class of drugs.

Barbiturates have enjoyed a long period of extensive use as sedative-hypnotic drugs. However, except for a few specialized uses, they have been largely replaced by the somewhat safer benzodiazepines.

The barbiturates reversibly depress the activity of all excitable tissues. Not all tissues are affected at the same dose or concentration. The CNS is the most sensitive to the action of barbiturates. When barbiturates are given in sedative or even hypnotic doses, there is very little effect on skeletal, cardiac, or smooth muscle. Even in anesthetic concentrations, peripheral effects are weak and do not create difficulties if the duration of anesthesia is not prolonged. However, if depression is extended, serious deficits in cardiovascular and other peripheral functions can occur.

Barbituric acid (2,4,6-trioxohexahydropyrimidine) and its analog thiobarbituric acid, lack central depressant activity, but the presence of alkyl or aryl groups at position-5 confers sedative-hypnotic and sometimes other activities. The general structural formula for the barbiturates and the structures of some of those available in the United States are shown in Table 1.

TABLE I

NAMES AND STRUCTURES OF SOME BARBITURATES AVAILABLE IN THE UNITED STATES

[Structure: barbiturate ring with $R_3$*, (S)**, $R_{5a}$, $R_{5b}$]

| barbiturate | $R_{5a}$ | $R_{5b}$ |
| --- | --- | --- |
| Amobarbital | ethyl | isopentyl |
| Aprobarbital | allyl | isopropyl |
| Barbital | ethyl | ethyl |
| Butabarbital | ethyl | sec-butyl |
| Butalbital | allyl | isobutyl |
| Hexobarbital* | methyl | 1-cyclohexen-1-yl |
| Mephobarbital* | ethyl | phenyl |
| Metharbital* | ethyl | ethyl |
| Methohexital* | allyl | 1-methyl-2-pentynyl |
| Pentobarbital | ethyl | 1-methylbutyl |
| Phenobarbital | ethyl | phenyl |
| Secobarbital | allyl | 1-methylbutyl |
| Talbutal | allyl | sec-butyl |
| Thiamylal** | allyl | 1-methylbutyl |
| Thiopental** | ethyl | 1-methylbutyl |

*$R_3$ = H, except in hexobarbital, mephobarbital, metharbital, and methohexital, where it is replaced by $CH_3$.
**O, except in thiamylal and thiopental, where it is replaced by S.

The carbonyl group at position-2 has acidic properties because of its position between the two amido nitrogens, resulting in lactam-lactim tautomerization. The lactim ("enol") form is favored in alkaline solutions, resulting in water-soluble salts. The lactam ("keto") form does not dissolve readily in water, although it is quite soluble in non-polar solvents. Compounds in which the oxygen at C-2 is replaced by sulfur are called thiobarbiturates, which are more lipid-soluble than the corresponding barbiturates.

In general, structural changes that increase lipid solubility decrease duration of action, decrease latency to onset of activity, accelerate metabolic degradation, and often increase hypnotic potency. Introduction of polar groups such as ether, keto, hydroxyl, amino, or carboxyl groups into the alkyl side chains decreases lipid-solubility and abolishes hypnotic activity. Methylation of the N-1 atom increases lipid-solubility and shortens the duration of action.

Convulsant seizures occur in various chronic central nervous system (CNS) disorders, particularly epilepsies. These seizures are generally correlated with abnormal and excessive EEG (electroencephalogram) discharges. A variety of drugs have been used for treatment of these seizures. Many of the older drugs are structurally related to phenobarbital, for example, the hydantoins, the deoxybarbiturates, the oxazolidinediones and the succinimides. More recently developed anticonvulsant compounds include the benzodiazepines, iminostilbenes, and valproic acid (Porter R. J., Meldrum, B. S.[1992] "Antiepileptic drugs" Basic & Clinical Pharmacology, Katzung B. G., Ed., Appleton & Lange, Norwalk, Conn., $5^{th}$ Edition, pp. 331–349). Additional compounds, containing various types of chemical structures and having various pharmacological mechanisms of action are being developed because of their anticonvulsant activities (Trevor, A. J., Way, W. L. [1992] "Sedative-hypnotics" Basic & Clinical Pharmacology, Katzung, B. G., Ed., Appleton & Lange, Norwalk, Conn., $5^{th}$ Edition, pp. 306–319).

The anticonvulsant drugs currently available in the United States have several shortcomings as therapeutic agents. About one of every three patients does not obtain significant relief from seizures and a number of side-effects accompany the therapeutic effects obtained.

The intravenous route of administration is usually reserved for the management of convulsive emergencies and for general anesthesia. Barbiturates are bound to plasma albumin to various extents. Lipid solubility is the primary determinant of binding. They also partition into fat in proportion to their lipid solubility. Highly lipid-soluble barbiturates such as thiopental, methohexital, thiamylal, thiohexital, and hexobarbital, undergo a rapid, flow-limited uptake into the most vascular areas of the brain. Maximal uptake occurs within 30 seconds after administration. There is then a redistribution into less vascularized areas of the brain and into other tissues. For such drugs there is no correlation between duration of action and elimination half-life. The highly vascular kidneys, liver, and heart equilibrate almost as fast as does the brain, so that maximum tissue concentration occurs within 1 minute after injection. The less lipid-soluble barbiturates equilibrate much more slowly because their uptake is limited by membrane permeability and not by blood flow. Cerebral uptake is slower and as long as 20 minutes may be required for sleep to occur after intravenous administration of barbital or phenobarbital. At steady-state, highest concentrations are achieved in fat which then acts as a slow-release reservoir of drug.

All barbiturates are filtered by the renal glomerulus in proportion to their free concentration in the blood. Barbiturates with a high lipid/water partition coefficient not only are highly protein bound and therefore are poorly filtered, but also are readily reabsorbed from the lumen of the tubule. The burden of elimination is thus put on the drug-metabolizing systems. When renal excretion is impaired, barbiturates that depend upon the kidney for elimination may cause severe CNS and cardiovascular depression. Small amounts of barbiturates are also secreted in milk. Metabolism occurs only in the liver for oxybarbiturates and to a small extent in the kidney for thiobarbiturates. The metabolism processes are oxidative in nature, leading to metabolites that are more polar and therefore more rapidly eliminated. The exception is the oxidative N-demethylation that leads to an active metabolite. The oxidative metabolism occurs mainly at carbon-5 where oxidation of radicals form alcohols, ketones, phenols, or carboxylic acids which may appear in the urine as such or as glucuronic acid conjugates. This process generally terminates biological activity.

Drug toxicity is an important consideration in the treatment of humans and animals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

Drug elimination is typically the result of metabolic activity upon the drug and the subsequent excretion of the drug from the body. Metabolic activity can take place within the vascular supply and/or within cellular compartments or organs. The liver is a principal site of drug metabolism. The metabolic process can be categorized into synthetic and nonsynthetic reactions. In nonsynthetic reactions, the drug is chemically altered by oxidation. reduction, hydrolysis, or any combination of the aforementioned processes. These processes are collectively referred to as Phase I reactions.

In Phase II reactions, also known as synthetic reactions or conjugations, the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

Absorption and redistribution are critical determinants of the time of onset and duration of anesthetic and hypnotic effects of ultrashort- and short-acting barbiturates. But it is the elimination rate that determines the time course of residual effects and accumulation of the drug during repetitive uses. Of all barbiturates currently used in the United States for hypnosis, only hexobarbital has a half-life of elimination that is sufficiently short (2.7–7 hours) for virtually complete elimination to occur within 24 hours. All other barbiturates will accumulate during repetitive administrations unless appropriate adjustments to dosage are made. Persistence of the drug in plasma furthermore favors the development of tolerance and abuse.

There is a need in the art for ultrashort acting hypnotic barbituates.

BRIEF DESCRIPTION OF THE INVENTION

The subject invention provides novel hypnotic barbiturates. Advantageously, the subject invention provides compounds which are readily metabolized by the physiological metabolic drug detoxification systems. Specifically, in a preferred embodiment, the therapeutic compounds of the subject invention contain a moiety, such as an ester group, which does not detract from the ability of these compounds to provide a therapeutic benefit, but which makes these compounds more susceptible to degradation by hydrolases, particularly serum and/or cytosolic esterases. Because these barbiturates are readily metabolized they are both highly effective and short acting. Their metabolism rate is not limited by renal filtration or hepatic uptake, but is controllable, predictable, and very rapid.

Degradation of the compounds of the subject invention by enzymes such as hydrolases (esterases, peptidases, lipases, glycosidases, phosphatases, etc.) is particularly advantageous for drug metabolism because these enzymes are ubiquitously distributed and their activity is not dependent on age, gender, or disease state to the same extent as oxidative hepatic drug metabolism.

In a preferred embodiment, the major metabolite of the compounds of the subject invention is a polar, water soluble carboxylate salt which is biologically inactive and rapidly cleared by the kidneys. Because the subject compounds are degraded by ubiquitous hydrolases, such as esterases, the compounds are ultra-short-acting hypnotic barbiturates with rapid clearance from the body, and little, if any, of the after-effects usually seen with presently available barbiturates. Their onset of activity is governed by their lipid solubility, as in currently used barbiturates. In addition, because the active drug does not persist in the plasma, the development of tolerance and abuse is less likely to happen.

The subject invention further provides methods of treatment comprising the administration of the compounds of the subject invention to individuals in need of treatment with hypnotic barbiturates.

The subject invention further provides compositions and methods useful to treat convulsions.

In a further embodiment, the subject invention pertains to the breakdown products which are formed when the therapeutic compounds of the subject invention are acted upon by hydrolases. The major metabolites of the compounds of the subject invention are polar, water soluble carboxylate salts. These metabolites are biologically inactive and rapidly cleared by the kidneys. These breakdown products can be used as described herein to monitor the clearance of the therapeutic compounds from a patient.

In yet a further embodiment, the subject invention provides methods for synthesizing the therapeutic compounds of the subject invention.

DETAILED DISCLOSURE

Figure 1:
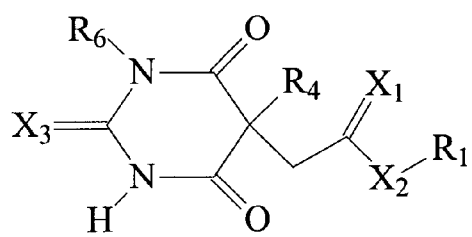
FIG. 1 describes the first series of compounds where R is an alkyl or an aryl residue containing 1 to about 14 carbon atoms, either linear or branched.

In one embodiment, the subject invention provides new and advantageous hypnotic barbiturates. Advantageously, the therapeutic compounds of the subject invention are stable in storage but have a shorter half-life in the physiological environment than other barbiturates; therefore, the compounds of the subject invention can be used with a lower incidence of side effects and toxicity.

A further aspect of the subject invention is the provision of compounds and compositions useful as anticonvulsants. Compounds of Formula I and/or Formula II (shown below) can be used for this purpose.

Specifically exemplified herein are compounds having the general chemical structure shown in Table I, with the exception that a moiety susceptible to degradation by hydrolases is introduced.

In one embodiment, as illustrated by Formula I, the moiety is introduced at the C5 position:

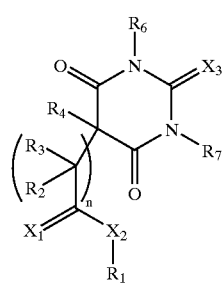

I where $R_1$ hydrogen or (saturated or unsaturated, branched or unbranched) $C_{1-14}$ alkyl or a (substituted or unsubstituted) aryl group. Non-limiting examples include methyl, ethyl, propyl, isopropyl, butyl, isobutyl, sec-butyl, ter-butyl, pentyl, isopentyl, neopentyl, cyclohexyl, benzyl, toluyl, menthyl, nor-bornyl, bornyl, and adamantanemethyl. $R_2$ and $R_3$ are, independently, hydrogen or (saturated or unsaturated, branched or unbranched) $C_{1-4}$ alkyl. $R_4$ is hydrogen or (saturated or unsaturated, branched or unbranched) $C_{1-14}$ alkyl or a (substituted or unsubstituted) aryl group. $R_6$ and $R_7$ are, independently, hydrogen or (saturated or unsaturated, branched or unbranched) $C_{1-14}$ alkyl. $X_1$, $X_2$, and $X_3$ are, independently, oxygen, nitrogen, or sulfur. Preferably, $X_3$ is oxygen or sulfur. Finally, n is an integer of from 0 and 5, preferably from 0 and 3, and more preferably 0 or 1.

In another embodiment, one example of which is illustrated by Formula II, the moiety is introduced on one of the nitrogen atoms:

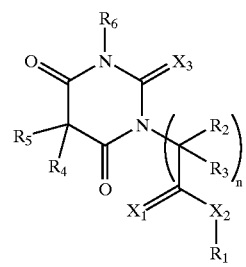

II where $R_1$ is hydrogen or (saturated or unsaturated, branched or unbranched) $C_{1-14}$ alkyl or a (substituted or unsubstituted) aryl group. Non-limiting examples include methyl, ethyl, propyl, isopropyl, butyl, isobutyl, sec-butyl, ter-butyl, pentyl, isopentyl, neopentyl, cyclohexyl, benzyl, toluyl, menthyl, nor-bornyl, bornyl, and adamantanemethyl. $R_2$ and $R_3$ are, independently, hydrogen or (saturated or unsaturated, branched or unbranched) $C_{1-4}$ alkyl. $R_6$ is hydrogen or (saturated or unsaturated, branched or unbranched) $C_{1-14}$ alkyl. Alternatively, as would be appreciated by one skilled in the art having the benefit of the instant disclosure, the substituent shown in Formula II could be on the other nitrogen with $R_6$ then being on the nitrogen which is shown in Formula II as being substituted. $R_4$ and $R_5$ are, independently, hydrogen or (saturated or unsaturated, branched or unbranched) $C_{1-14}$ alkyl or a (substituted or unsubstituted) aryl group. Examples include ethyl, allyl, phenyl, 1-methylbutyl, sec-butyl, isobutyl, 2-cyclopentenyl, 1-cyclohexen-1-yl, 1-methyl-2-pentynyl, isopentyl, neopentyl, cyclohexyl, benzyl. toluyl, menthyl, nor-bornyl, bornyl, or adamantanemethyl. $X_1$, $X_2$, and $X_3$ are, independently, oxygen, nitrogen, or sulfur. Preferably, $X_3$ is oxygen or sulfur. Finally, n is an integer of from 0 and 5, preferably from 0 to 3, and most preferably 0 or 1.

As would be appreciated by one skilled in the art, the alkyl and/or aryl groups on the compounds of the subject invention could be substituted with a variety of different moieties, so long as the substitutions do not detract from the desired biological activity of the compounds. Thus, the alkyl and aryl groups may be substituted with, for example, $C_{1-10}$ alkyl, substituted alkyl groups, substituted or unsubstituted carboxylic acids, substituted or unsubstituted carboxylic esters, halogen, carboxyl, hydroxyl, phosphate, phosphonate, aryl, CN, OH, COOH, $NO_2$, $NH_2$, $SO_{2-4}$, $C_{1-20}$ heteroalkyl, $C_{2-20}$ alkenyl, alkynyl, akynyl-aryl, alkynyl-heteroaryl, aryl, $C_{1-20}$ alkyl-aryl, $C_{2-20}$ alkenyl-aryl, heteroaryl, $C_{1-20}$ alkyl-heteroaryl, $C_{2-20}$ alkenyl-heteroaryl, cycloalkyl, heterocycloalkyl, $C_{1-20}$ alkyl-heteroycloalkyl, and $C_{2-20}$ alkyl-cycloalkyl, any of which may be, optionally, substituted with a moiety selected from the group consisting of $C_{1-6}$ alkyl, halogen, OH, $NH_2$, CN, $NO_2$, COOH, or $SO_{2-4}$ Compounds of Formula I are particularly preferred for anticonvulsant activity while compounds of Formula III are particularly preferred for sedative-hypnotic applications.

Advantageously, the presence of a hydrolyzable group in the molecule makes these compounds biodegradable by. for example, blood and tissue esterases, yielding a carboxylic acid metabolite that is water soluble at physiological pH and therefore rapidly eliminated by renal filtration. This, in turn, alleviates the after-effects usually observed in patients receiving hypnotic barbiturates. Accordingly, in a specific embodiment, the subject invention provides esterified hypnotic barbiturates and compositions of these esterified compounds.

FIG. 1 shows a first series of compounds of Formula I of the subject invention where $R_1$ is an alkyl or an aryl residue containing 1 to about 14 carbon atoms, either linear or branched. In this series $R_6$ is a hydrogen, a methyl or an ethyl group. $R_4$ is alkyl or aryl having between 1 and about 14 carbon atoms. $X_3$ is oxygen or sulfur. Finally, n is an integer of from 0 and 5, preferably from 0 to 3, and most preferably 0 or 1.

Figure 2:
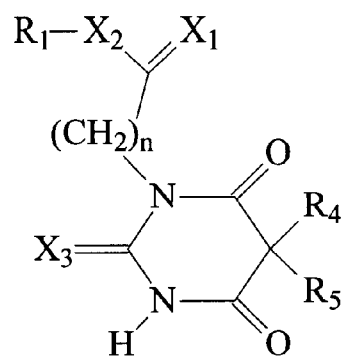
FIG. 2 describes the other series of compounds where R is an alkyl or an aryl residue containing 1 to about 14 carbon atoms, either linear or branched.

FIG. 2 shows another series of compounds of the subject invention where $R_1$ is an alkyl or an aryl residue containing 1 to about 14 carbon atoms, either linear or branched. In this series, $R_4$ is ethyl or allyl. $R_5$ is alkyl or aryl having between 1 and about 14 carbon atoms. $X_3$ is oxygen or sulfur. Finally, n is an integer of from 0 and 5, preferably from 0 and 3, and more preferably 0 or 1.

In a specific embodiment, the compounds of this invention are thiobarbiturates, i.e., the 2-position is a thione as shown in Formla III(below). In a preferred embodiment, the compounds of the subject invention are substituted at one of the nitrogens, such as position-1. Alternatively, as discussed above, the compounds could be substituted at the C5 position. The substituent contains a group that is readily cleaved by a non-oxidative hydrolytic enzyme. The presence of this group makes these compounds biodegradable by blood and tissue enzymes, yielding a metabolite that is water soluble at physiological pH and therefore rapidly eliminated by renal filtration. This in turn alleviates the after-effects usually observed in patients receiving hypnotic barbiturates.

Thus, in one embodiment, the compounds of the subject invention have the following structure:

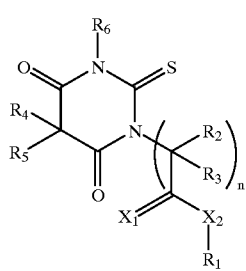

III

Wherein:
$R_1$ is hydrogen or an alkyl or an aryl group containing 1 to about 14 carbon atoms, either linear or branched, substituted or unsubstituted. Preferred examples are compounds where $R_1$ is phenyl, benzyl, methyl, ethyl, propyl, isopropyl, butyl, isobutyl, sec-butyl, ter-butyl, pentyl, isopentyl, neopentyl, cyclohexyl, benzyl, toluyl, menthyl, nor-bornyl, bornyl, lauryl, myristyl, or adamantanemethyl.

$X_1$ and $X_2$ are, independently, O, S, or N.

$R_4$ and $R_5$ are, independently, saturated or unsaturated alkyl or aryl having between 1 and about 14 carbon atoms. Preferred examples are ethyl, allyl, phenyl, benzyl, 1-methylbutyl, sec-butyl, isobutyl, 2-cyclopentenyl, 1-cyclohexen-1-yl, 1-methyl-2-pentynyl, isopentyl, and neopentyl.

$R_6$ is hydrogen or alkyl having between 1 and about 14 carbon atoms. Preferably, $R_6$ is hydrogen, methyl, or ethyl. Most preferably, $R_6$ is hydrogen.

Finally, n is an integer of from 0 and 5, preferably from 0 and 3, and more preferably 0 or 1.

In a preferred embodiment of the subject invention, hypnotic barbiturates are provided which contain an ester group which is acted upon by estarases thereby breaking down the compound and facilitating its efficient removal from the treated individual. In a preferred embodiment the therapeutic compounds are metabolized by the Phase I drug detoxification system.

This invention includes pharmaceutical compositions comprising any of the compounds of Formulas I and II (or analogs thereof), alone or in combination with each other or other active compounds, in an amount effective for providing hypnotic barbiturate effect and/or ameliorating convulsions or the symptoms of convulsions or in an amount effective for ameliorating anxiety or its symptoms. Pharmaceutical compositions of this invention include various pharmaceutical dosage forms formulated for oral or transdermal administration or administration by injection to a mammal and include among others, tablets, pills, capsules, and injectable solutions or suspensions. Pharmaceutical compositions of this invention contain from about 0.1% to about 99% of one or more compounds of Formula I or II (or an analog thereof). The pharmaceutical compositions preferably include those that contain from about 1% to about 90% of one or more of the compounds of Formula I or II.

This invention is also directed to methods of providing a hypnotic barbiturate effect and/or preventing or treating convulant seizures in mammals, by administration to the mammal of an amount of a compound of Formula I or II (or an analog thereof) effective for preventing or ameliorating convulsant seizures or the symptoms of such seizures. This invention is further directed to methods of preventing or treating anxiety in mammals by administration to the mammal of an amount of a compound of Formula I or II (or an analog thereof) or mixtures thereof effective for preventing or ameliorating anxiety or the symptoms of anxiety. Administration can be by any known route including, but not limited to, injection or oral or transdermal routes.

The anticonvulsant properties can be confirmed by pharmacologic testing, utilizing two standard animal models of epilepsy: the pentylenetetrazole (PTZ)-induced seizure procedure and the maximal electroshock test (MES). General descriptions of such testing can be found in J. F. Reinhard and J. F. Reinhard, Jr., "Experimental Evaluation of Anticonvulsants" in Anticonvulsants, J. A. Vida, Ed., Academic Press, New York, N.Y., 1977.

In general, compounds may be used in treating epilepsy in mammals including humans. Medical aspects of the treating of epilepsy are described in greater detail by Rail and Schleifer in Goodman and gilman's The Pharmacological Basis of Therapeutics, 8$^{th}$ Ed.; Goodman Gilman, A.; Rail, T. W.; Nies, A. S.; Taylor, P., Eds.; Pergamon Press: New York, 1990; pp. 436–462.

A further aspect of the subject invention pertains to the breakdown products which are produced when the therapeutic compounds of the subject invention are acted upon by hydrolases. The presence of these breakdown products in the urine or serum can be used to monitor the rate of clearance of the therapeutic compound from a patient.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site which is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, 54$^{th}$ Ed., Medical Economics Company, Montvale, N.J., 2000).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention are formulated such that an effective amount of the bioactive compound(s) is combined with a suitable carrier in order to facilitate effective administration of the composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be, for example a mouse, rat, pig, horse, rabbit, goat, pig, cow, cat, dog, or human. In a preferred embodiment, the individual is a human.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl, $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

Figure 3:
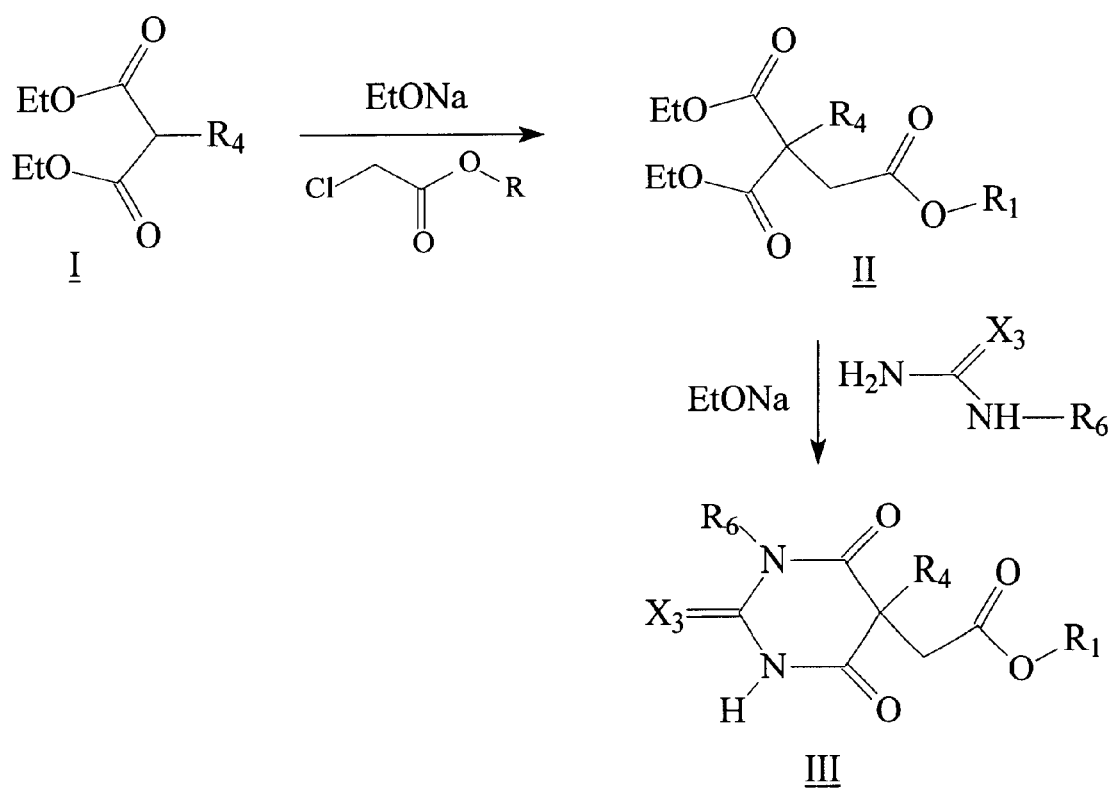
FIG. 3 depicts the synthesis of the series of compounds shown in FIG. 1.
Figure 4:
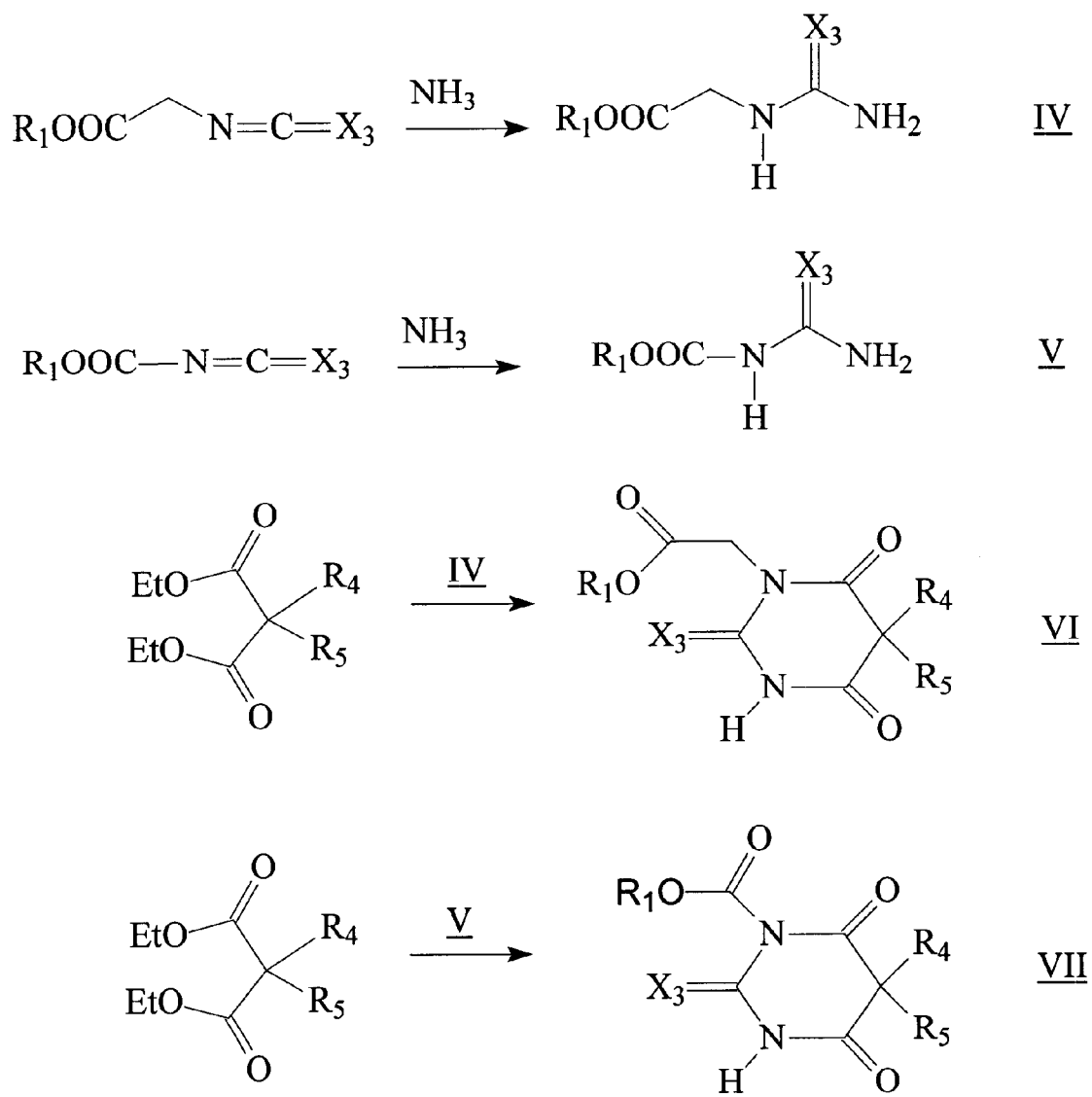
FIG. 4 depicts the synthesis of the series of compounds shown in FIG. 2.

The synthesis of certain compounds of the subject invention is described in FIGS. 3 and 4. The synthesis of series 1 (FIG. 1) is described in FIG. 3, where a substituted diethyl malonate compound is deprotonated by sodium ethoxide in ethanol and reacted with an ester of chloroacetic acid in order to give the intermediate II. This intermediate is in turn condensed with an N-substituted urea or thiourea in ethanol/sodium ethoxide in order to yield the desired product III. Synthesis of series 2 (FIG. 2) is described in FIG. 4. In this series, an alkyl iso(thio)cyanatoacetate or an alkyl iso(thio)cyanate is reacted with ammonia in order to form the corresponding urea (thiourea) IV or V, respectively. These in turn are reacted with a disubstituted diethyl malonate in order to yield the desired compounds.

Figure 5:
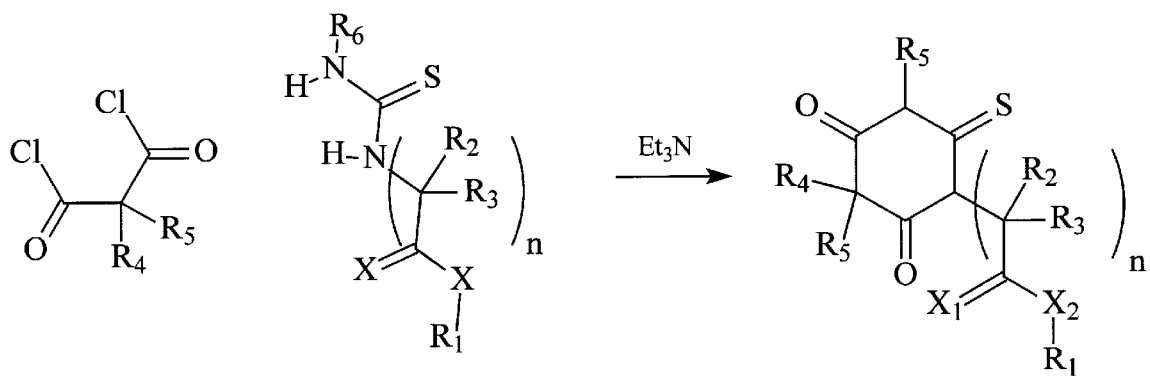
FIG. 5 shows the synthesis of certain thiobarbiturates of the subject invention.
Figure 6:
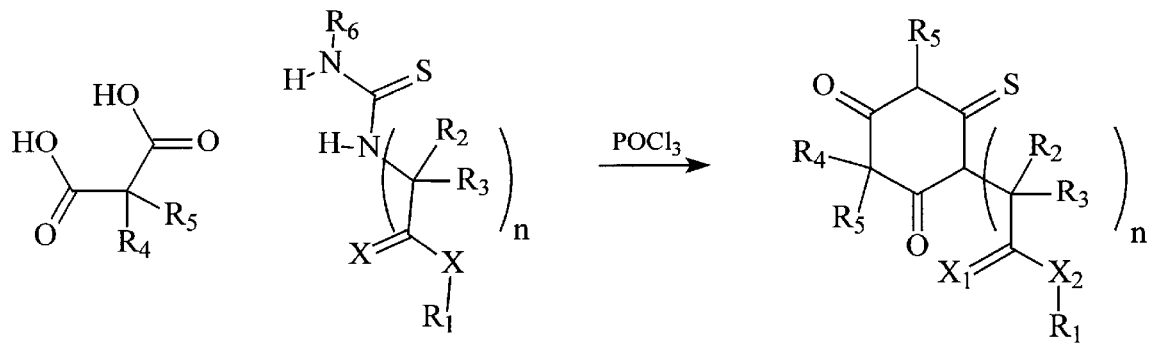
FIG. 6 shows the synthesis of additional compounds of the subject invention.

The synthesis of certain thiobarbituates of the subject invention is described in FIG. 5. where a 2,2-disubstituted malonyl chloride reacts with a N-substituted or a N,N-disubstituted thiourea to give the compounds of this invention. Alternatively, as shown in FIG. 6, a 2,2-disubstituted malonic acid reacts with the substituted thiourea in the presence of phosphorus oxychloride to give compounds of this invention. In a closely related synthetic method, acetic anhydride can be substituted for phosphorus oxychloride, thus giving again the desired thiobarbiturate product.

Figure 7:
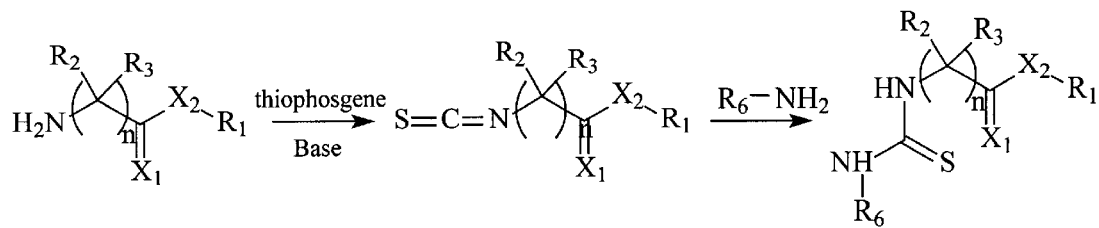
FIG. 7 shows the synthesis of a substituted thiourea.

The synthesis of a substituted thiourea is described in FIG. 7, where a γ-aminoacid ester reacts with thiophosgene in the presence of a base such as triethylamine in methylene chloride, or such as sodium bicarbonate in a methylene chloride/water biphasic system to give a isothiocyanatoalkylcarboxylate ester. The aqueous phase can also be omitted, and the reaction can take place in a suspension of calcium carbonate in methylene chloride. In a typical procedure, 2 equivalents of thiophosgene in toluene or dichloromethane is added to an iced-cooled solution of the aminoacid in methylene chloride containing calcium carbonate as a solid. The reaction is usually complete after 10 to 30 minutes of rapid stirring.

The synthesis of the 2,2-disubstituted malonyl chloride compounds used according to the subject invention can be done according to well known procedures. Typically, diethyl malonate is alkylated at the 2-position using 1 equivalent of sodium ethoxide as a base and 1 equivalent of an alkyl halide in ethanol. The resulting monoalkylated product can then be alkylated again using another equivalent of sodium ethoxide and another equivalent of an alkyl halide in ethanol. The resulting 2,2-disubstituted diethyl malonate is then hydrolyzed to the diacid using 2 equivalents of lithium hydroxide in ethanol/water. The product is isolated as a dicarboxylic acid upon acidification with dilute HCl or with citric acid.

This diacid in turn is reacted with phosphorus pentachloride to give the 2,2-disubstituted malonyl chloride used in the synthesis of the thiobarbiturates.

Materials and Methods

Reagents were bought from Aldrich Chemical Company (Milwaukee, Wis.) unless stated otherwise. Diethyl $\Delta^2$-cyclopentylmalonate was prepared according to the procedure described in Organic Syntheses IV:29I.

Following are examples which illustrate procedures for practicing the invention. These examples should not be construed as limiting. All percentages are by weight and all solvent mixture proportions are by volume unless otherwise noted.

EXAMPLE 1

Esters of Chloroacetic Acid

Adamantanemethyl chloroacetate 1, neopentyl chloroacetate 2, isobutyl chloroacetate 3, and cyclohexyl chloroacetate 4 were prepared as follows: To a solution of chloroacetyl chloride (10 mmoles) in dry methylene chloride was added an equimolar amount of either adamantanemethanol, neopentanol, isobutanol, or cyclohexanol. After 2 hours at room temperature the solvent was removed and the product was distilled under reduced pressure to give a colorless liquid.

EXAMPLE 2

Esters of Diethyl Phenylmalonylacetic Acid

Adamantanemethyl, neopentyl, isobutyl, and cyclohexyl esters 5,6,7, and 8, respectively were prepared as follows: To 0.1 mole of sodium ethoxide in absolute ethanol (200 ml) was added 0.1 moles of diethyl phenylmalonic acid followed by 0.1 mole of the appropriate ester of chloroacetic acid described above. After refluxing for 4 hours, the mixture was filtered and the solvent was evaporated. The product was recrystallized from hot ethanol.

EXAMPLE 3

Esters of Diethyl $\Delta^2$-cyclopentylmalonylacetic Acid

Adamantanemethyl, neopentyl, isobutyl, and cyclohexyl esters 9,10,11, and 12, respectively were prepared as follows: To 0.1 mole of sodium ethoxide in absolute ethanol (200 ml) was added 0.1 moles of diethyl $\Delta^2$-cyclopentylmalonic acid followed by 0.1 mole of the appropriate ester of chloroacetic acid described above. After refluxing for 4 hours, the mixture was filtered and the solvent was evaporated. The product was recrystallized from hot ethanol.

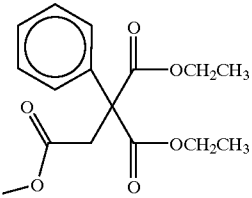

| | | |
|---|---|---|
| 5 | R = adamantanemethyl | 9 |
| 6 | R = neopentyl | 10 |
| 7 | R = isobutyl | 11 |
| 8 | R = cyclohexyl | 12 |

EXAMPLE 4

3-Methyl-4,6-dioxo-5-phenylhexahydropyrimidine-5-acetic Acid, Adamantanemethyl Ester: 13

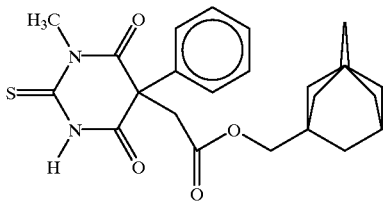

To 0.1 mole of sodium ethoxide in absolute ethanol is added 0.1 mole of the ester 5 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in in vacuo.

EXAMPLE 5

3-Methyl-4,6-dioxo-5-phenylhexahydropyrimidine-5-acetic Acid, Neopentyl Ester: 14

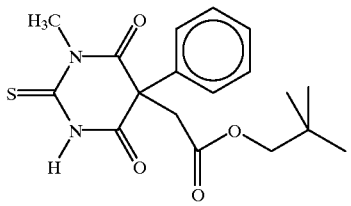

To 0.1 mole of sodium ethoxide in absolute ethanol is added 0.1 mole of the ester 6 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 6

3-Methyl-4,6-dioxo-5-phenylhexahydropyrimidine-5-acetic Acid, Isobutyl Ester: 15

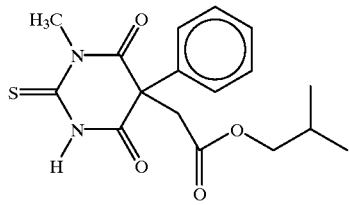

To 0.1 mole of sodium ethoxide in absolute ethanol is added 0.1 mole of the ester 7 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 7

3-Methyl-4,6-dioxo-5 Phenylhexahydropyrimidine-5-acetic Acid, Cyclohexyl Ester: 16

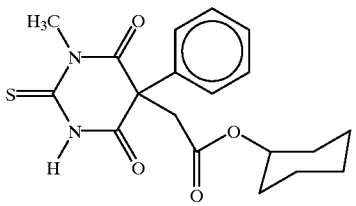

To 0.1 mole of sodium ethoxide in absolute ethanol is added 0.1 mole of the ester 8 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 8

3-Methyl-4,6-dioxo-5-$\delta^2$-cyclopentylhexahydropyrimidine-5-acetic Acid Adamantanemethyl Ester: 17

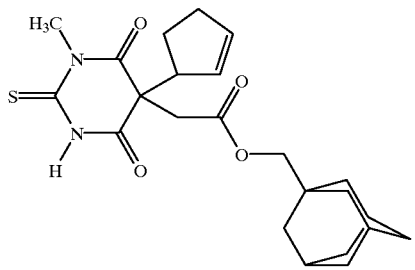

To 0.1 mole of sodium ethoxide in absolute ethanol is added 0.1 mole of the ester 9 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 9

3-Methyl-4,6-dioxo-5-$\delta^2$-cyclopentylhexahydropyrimidine-5-acetic Acid Neopentyl Ester: 18

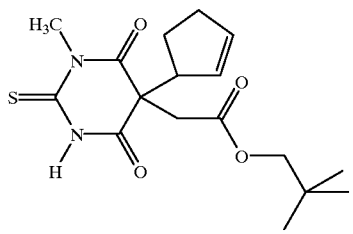

To 0.1 mole of sodium ethoxide in absolute ethanol is added 0.1 mole of the ester 10 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 10

3-Methyl-4,6-dioxo-5-$\delta^2$-cyclopentylhexahydropyrimidine-5-acetic Acid Isobutyl Ester: 19

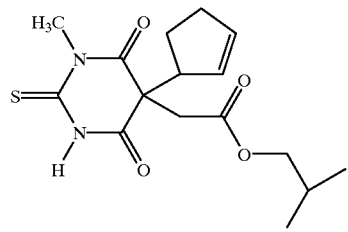

To 0.1 mole of sodium ethoxide in absolute ethanol is added 0.1 mole of the ester 11 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 11

3-Methyl-4,6-dioxo-5-δ²-cyclopentylhexahydropyrimidine-5-acetic Acid Cyclohexyl Ester: 20

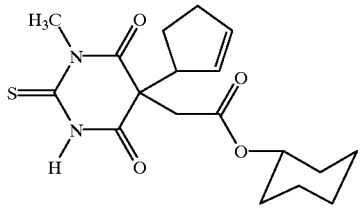

To 0.1 mole of sodium ethoxide in absolute ethanol is added 0.1 mole of the ester 12 followed by 0.1 mole of dry N-methylthiourea in hot absolute ethanol. After refluxing for 8 hours, hot water (500 ml) is added, followed by enough HCl to make the solution acidic. The solution is then filtered and cooled in an ice-bath overnight. The white product is collected by filtration and dried in vacuo.

EXAMPLE 12

Thiourea (N-acetic Acid Ethyl Ester): 21

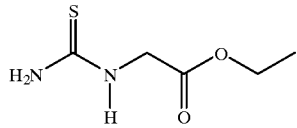

To 0.1 mole of ethyl isothiocyanatoacetate in ethanol (50 ml) is added 50 ml of a 2M ethanolic solution of ammonia. After 2 hours at room temperature, the precipitated product is collected by filtration and used in the next step.

EXAMPLE 13

N-ethoxycarbonylthiourea: 2

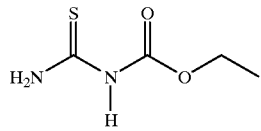

To 0.1 mole of ethoxycarbonyl isothiocyanate in ethanol (50 ml) is added 50 ml of a 2M ethanolic solution of ammonia. After 2 hours at room temperature, the precipitated product is collected by filtration and used in the next step.

EXAMPLE 14

4,6-Dioxo-5-allyl-5-isopentylhexahydropyrimidine-3-aceticacid, Ethyl Ester: 23

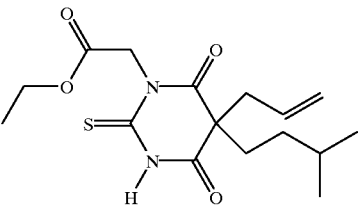

Compound 21 (10 mmoles) is dissolved in ethanol containing 10 mmoles of sodium ethoxide. To this is added 10 mmoles of diethyl (allylisopentyl)malonate and the mixture is refluxed for 8 hours. The product crystallized upon cooling.

EXAMPLE 15

3-Ethoxycarbonyl-4,6-dioxo-5-allyl-5-isopentylhexahydropyrimidine 24

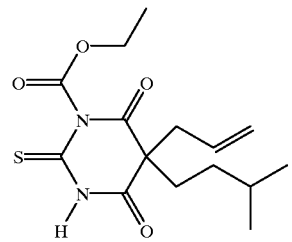

Compound 22 (10 mmoles) is dissolved in ethanol containing 10 mmoles of sodium ethoxide. To this is added 10 mmoles of diethyl (allylisopentyl)malonate and the mixture is refluxed for 8 hours. The product crystallized upon cooling.

EXAMPLE 16

Hypnotic Activity in Rats

When compounds 13 to 20, 23 and 24 are administered to rats intraperitoneally at a dose of 50 mg/kg, they induce sleep within 10 minutes after administration. The hypnosis is of short duration (less than one hour), consistent with the scope of this invention.

EXAMPLE 17

2-Thiohydantoin 9.89 g of Glycine methyl ester, hydrochloride salt, and 6.9 g of potassium thiocyanate are heated at 150° C. in an oil bath with occasional stirring for 15 minutes or until a brownish melt is obtained. The reaction is cooled down and 100 ml of ethanol is added. Stir at room temperature for 4 hours. Filter off the precipitate and wash it with ethanol. The filtrate is evaporated and the residue is crystallized from acetone and methyl ter-butyl ether.

EXAMPLE 18

1-Carboxymethylthiourea 5.8 g of 2-Thiohydantoin and 15 g of barium hydroxide hydrate are refluxed in 200 ml of water for 1 hour. The mixture is cooled in an ice bath and acidified to pH 2.0 with 10% sulfuric acid. Filter through celite. The filtrate is then continuously extracted for 2 days with ethyl ether. The extract is evaporated and the residual water is removed by co-distillation with methanol/ethyl acetate. The product is then crystallized from methanol/ethyl acetate.

EXAMPLE 19

General Method for the Preparation of Isothiocyanato-γ-alkylcarboxylate Esters The γ-aminoalkylcarboxylate ester and 1.1 equivalent amount of thiophosgene are added to a stirring mixture of methylene chloride (100 ml) and saturated sodium bicarbonate solution (100 ml). After stirring for 2 hours, the organic phase is washed with 100 ml water, dried over magnesium sulfate, and evaporated. The yield of product is nearly quantitative. The following compounds were prepared from this method:

Methyl isothiocyanato-2-acetate (from glycine methyl ester, HCl)

Ethyl isothiocyanato-2-acetate from glycine ethyl ester, HCl)

Neopentyl isothiocyanato-2-acetate (from glycine neopentyl ester, HCl)

Nor-Bornyl isothiocyanato-2-acetate (from glycine Norbornyl ester, HCl)

Methyl isothiocyanato-4-butyrate (from 4-amninobutyric acid methyl ester, HCl)

Methyl isothiocyanato-2-methyl-2-propionate (from 2-amino-2-methylpropionic acid methyl ester, HCl)

Benzyl isothiocyanato-2-methyl-2-propionate (from 2-amino-2-methylpropionic acid benzyl ester, HCl)

Methyl isothiocyanato-2-propionate from alanine methyl ester, HCl)

ter-Butyl isothiocyanato-2-propionate from alanine ter-butyl ester, HCl)

ter-Butyl isothiocyanato-2-acetate from glycine ter-butyl ester, HCl)

Methyl isothiocyanato-12-laurate (from 12-amninolauric acid methyl ester, HCl)

Methyl isothiocyanato-2-myristate (from 14-aminotmyristic acid methyl ester, HCl)

Isothiocyanato-4-butyric acid amide from 4-aminobutyric acid amide)

Isothiocyanato-4-butyric acid N, N-dimethylamide (from 4-aminobutyric acid N,N-dimethylamide)

Isothiocyanato-4-butyric acid morpholinamide (from 4-aminobutyric acid morpholinamide)

EXAMPLE 20

General Method for the Preparation of the 1-substituted Thiourea

The isothiocyanatoalkyl carboxylate esters and amides described in example 3 are dissolved in THF and one equivalent amount of ammonia in methanol/water is added dropwise at 0° C. The solvent is evaporated and the residue is purified by flash chromatography through a short plug of silica. An example is given for the preparation of 1-Carbethoxymethylthiourea, where 2.3 of 28–30% Aqueous ammonia solution in 10ml of methanol is added dropwise to an ice-cooled solution of 5 g ethyl isothiocyanato-2-acetate in 50 ml of THF. The mixture is stirred at room temperature for another 2 hours and is evaporated. The residual water is removed by co-distillation with ethyl acetate and is filtered through a short plug of silica, eluting with methanol/methylene chloride 03:97. The product (4.83 g) is an orange solid.

EXAMPLE 21

General Method for the Preparation of 1-Substituted-thiobarbiturates

Equivalent amounts of 2,2-disubstituted malonyl chloride and 1-substituted thiourea are mixed and stirred at 80° C. overnight. The mixture is then diluted with water and extracted with an organic solvent. The crude product is either distilled or is precipitated by acidification of its sodium salt. The following are examples of compounds made after this procedure:

1-Carbethoxymethyl-5,5-diethylthiobarbituric acid: 39 g of Diethylmalonyl chloride is mixed with 64 g of 2-thiohydantoic acid ethyl ester. Heat at 80° C. for 18 hours. Cool down to room temperature and then dilute with 200 ml of water. Extract with dichloromethane and then evaporate the solvent. The oily residue is dissolved in 1N NaOH and is then precipitated out by slow addition of 1N HCl. The product is purified by solubilizing again in 1N NaOH and then precipitating it with 1N HCl.

1-carbethoxymethyl-5-ethyl-5-isoamylihio barbituric acid: 35 g of 2-Ethyl-2- isoamylmalonyl chloride, prepared from 2-ethyl-2-isoamylmalonic acid (52 g) and phosphorus pentachloride (148 g), and thiohydantoic acid ethyl ester are mixed and heated at 80° C. for 18 hours. Cool to room temperature and then pour into 200 ml of cold water. Extract with dichloromethane. Evaporate the solvent and then distill the oily residue at 1 mm Hg.

1-Carbethocyniethyl-5,5-dibutylthiobarbituric acid: 44 g of Dibutylmalonyl chloride is mixed with 64 g of 2-thiohydantoic acid ethyl ester and is stirred at 80C. for 18 hours. Cool down to room temperature and then dilute with 200 ml of water. Extract with dichloromethane and then evaporate the solvent. The oily residue is dissolved in 1N NaOH and is then precipitated out by slow addition of 1N HCl. The product is purified by solubilizing again in 1N NaOH and then precipitating it with IN HCl. The following compounds were also made after the same procedure:

1-carbomethoxytridecyl-5-ethyl-5-(2-pentyl)thiobarb ituric acid 1-carbornethoxyundecyl-5-ethyl-5-(2-pentyl) thiobarbituric acid 1-carbo(neopentyloxy)methyl-5,5-dibutylthiobarbituric acid 1-carbo(norbornyloxy)methyl-5-ethyl-5-isoamylthiobarbituric acid 1-(4-butyric acid morpholinamide)-5,5-dipropylthiobarbituric acid 1-(4-butyric acid amide)-5,5-dipropylthiobarbituric acid 1- (4-butyric acid N,N-dimeethylamnide)-5,5-dipropyl/thiobarbituric acid 1-(2-propionic acid ter-butyl ester)-5-ethyl-5-cyclopenty/thiobarbituric acid 1-(2-methyl-2-propionic acid benzyl ester)-5,5-dipropylthiobarbituric acid 1-carbomethoxy-5,5-dibutylthiobarbituric acid 1-carbomethoxy-5,5-dipropylthiobarbituric acid 1-carbomethoxy-5,5-diethylthiobarbituric acid 1-carbomethoxy-5-allyl-5-(2-pentyl)thiobarbituric acid 1-carbomethoxy-5-ethyl-5-(2-pentyl) thiobarbituric acid

EXAMPLE 22

Preparation of Salts

The thiobarbiturate is dissolved in an equivalent amount of 0.8N ethanolic sodium hydroxide solution. Most of the solvent is then evaporated and the salt is precipitated with hexane. Filter and wash with more hexane. Dry in vacuo.

It should be understood that the examples, reaction schemes, and embodiments described herein are for illustrative purposes only and that various modifications or changes in light thereof will be suggested to persons skilled in the art and are to be included within the spirit and purview of this application and the scope of the appended claims.

We claim:

1. A method for providing sedative-hypnotic treatment to an individual in need of such treatment wherein said method comprises administering to the individual an effective amount of a compound, or an analog thereof, wherein said compound has a structure selected from the group consisting of:

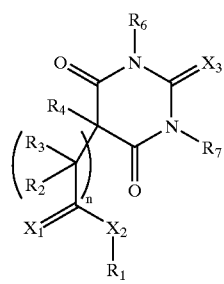

I where $R_1$ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N;

and

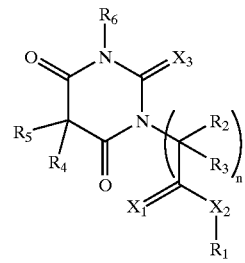

II where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ and $R_5$ are, independently, hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl;

$X_1$ and $X_2$ are, independently, O, S, or N; and $X_3$ is S or N.

2. The method, according to claim 1, wherein said compound has the following formula:

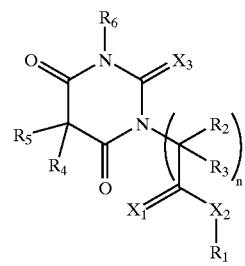

II where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ and $R_5$ are, independently, hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl;

$X_1$ and $X_2$ are, independently, O, S, or N; and $X_3$ is S or N.

3. The method, according to claim 2, wherein $X_3$=S.

4. The method, according to claim 3, wherein said compound has the following formula:

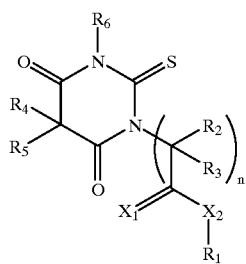

III where R₁ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ and $R_5$ are, independently, hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl;

$X_1$ and $X_2$ are, independently, O, S, or N; and $X_3$ is S or N.

5. The method, according to claim 4, wherein $R_1$, $R_4$ and $R_5$ are, independently, selected from the group consisting of: hydrogen, phenyl, benzyl, methyl, ethyl, propyl, isopropyl, butyl, isobutyl, sec-butyl, ter-butyl, pentyl, isopentyl, neopentyl, cyclohexyl, benzyl, toluyl, menthyl, nor-bornyl, bornyl, lauryl, myristyl, and adamantanemethyl.

6. The method, according to claim 4, wherein $R_6$=H.

7. The method, according to claim 4, wherein $R_1=R_2=R_3=R_4=R_5=R6=H$.

8. The method, according to claim 4, wherein $X_1=X_2=O$.

9. The method, according to claim 4, wherein n is 0 or 1.

10. The method, according to claim 1, wherein said individual is a human.

11. A method for providing anticonvulsant treatment to an individual in need of such treatment where said method comprises administering to the individual an effective amount of a compound, or an analog thereof, wherein said compound has a structure selected from the group consisting of:

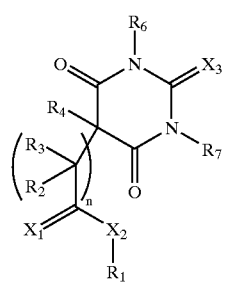

I where R₁ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N; and

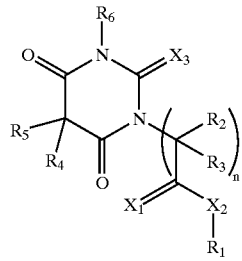

II where R₁ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl; and $X_1$, $X_2$ and $X_3$ are, independently, O, S, or N.

12. The method, according to claim 11, wherein said compound has the following formula:

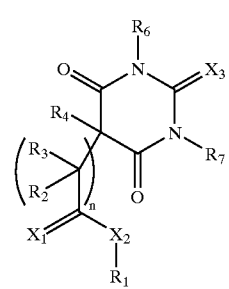

I where R₁ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N.

13. The method, according to claim 11, wherein said compound has the following formula:

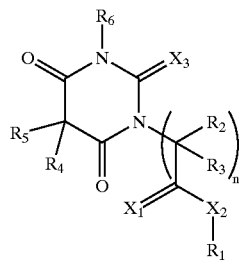

II where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl; and $X_1$, $X_2$ and $X_3$ are, independently, O, S, or N.

14. The method, according to claim 12, wherein $R_2=R_3=R_4=R_6=R_7=H$.

15. The method, according to claim 12, wherein $X_1=X_2=O$.

16. The method, according to claim 13, wherein $X_3=S$.

17. The method, according to claim 16, wherein said compound has the following formula:

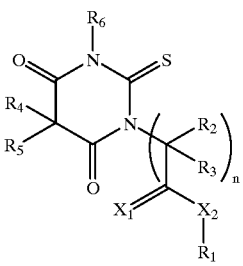

III where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ and $R_5$ are, independently, is hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl;

$X_1$, and $X_2$ are, independently, O, S, or N; and $X_3$ is S or N.

18. The method, according to claim 17, wherein $R_1=R_2=R_3=R_4=R_5=R_6=H$.

19. The method, according to claim 17, wherein $X_1=X_2=O$.

20. The method, according to claim 11, wherein said individual is a human.

21. A pharmaceutical composition comprising a compound, or an analog thereof, wherein said compound has a structure selected from the group consisting of:

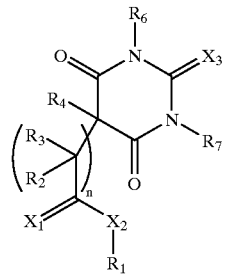

I where $R_1$ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N; and

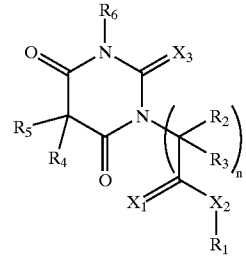

II where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substitutued or unsubstituted) aryl group;

$R_6$ is hydrogen or (saturated or unsaturated, branched or unbranched) $C_{1-14}$ alkyl;

$X_1$ and $X_2$ are, independently, O, S, N; and $X_3$ is S or N; and wherein said composition further comprises a pharmaceutically acceptable carrier.

22. The composition, according to claim 21, wherein said compound has the following formula:

I

[Structure I: barbiturate-like ring with R6 on N, X3, R7 on N, R4, R3, R2, n, X1, X2, R1]

where $R_1$ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N.

23. The composition, according to claim 21, wherein said compound has the following formula:

II

[Structure II]

where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl; and $X_1$, $X_2$ and $X_3$ are, independently, O, S, or N.

24. The composition, according to claim 22, wherein $R_2=R_3=R_4=R_6=R_7=H$.

25. The composition, according to claim 22, wherein $X_1=X_2=O$.

26. The composition, according to claim 23, wherein $X_3=S$.

27. The composition, according to claim 26, wherein said compound has the following formula:

III

[Structure III]

28. The composition, according to claim 27, wherein $R_1=R_2=R_3=R_4=R_5=R_6=H$.

29. The composition, according to claim 27, wherein $X_1=X_2=O$.

30. A compound, or an analog thereof, wherein said compound has a structure selected from the group consisting of:

I

[Structure I]

where $R_1$ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N; and

II

[Structure II]

where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ is hydrogen or (saturated or unsaturated, branched or unbranched) $C_{1-14}$ alkyl;

$X_1$ and $X_2$ are, independently, O, S, or N; and $X_3$ is S or N.

31. The compound, according to claim 30, which has the following formula:

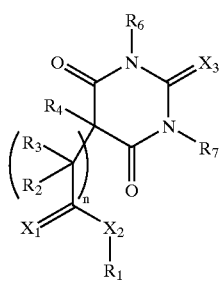

I where $R_1$ is hydrogen or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

$R_6$ and $R_7$ are, independently, hydrogen or (saturated or unsaturated, branched or unbranched) $C_{1-14}$ alkyl; and $X_1$, $X_2$ and $X_3$ are, independently, O, S, or N.

32. The compound, according to claim 30, which has the following formula:

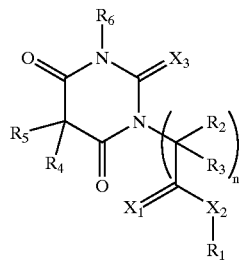

II where $R_1$ is hydrogen, or (saturated or unsaturated, branched or unbranched) $C_{1-14}$ alkyl or a (substituted or unsubstituted) aryl group;

$R_2$ and $R_3$ are, independently, hydrogen or (saturated or unsaturated, branched or unbranched) $C_{1-4}$ alkyl, and n is 0 to 5;

$R_4$ is hydrogen or (saturated or unsaturated, branched or unbranched) $C_{1-14}$ alkyl or a (substituted or unsubstituted) aryl group;

R6 is hydrogen or (saturated or unsaturated, branched or unbranched) $C_{1-14}$ alkyl; and $X_1$, $X_2$ and $X_3$ are, independently, O, S, or N.

33. The compound, according to claim 31, wherein $R_2=R_3=R_4=R_6=R_7=H$.

34. The compound, according to claim 31, wherein $X_1=X_2=O$.

35. The compound, according to claim 32, wherein $X_3=S$.

36. The compound according to claim 35, which has the following formula:

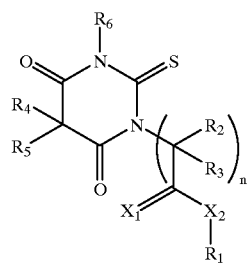

III

37. The compound, according to claim 36, wherein $R_1=R_2=R_3=R_4=R_5=R_6=H$.

38. The compound according to claim 36, wherein $X_1=X_2=O$.

* * * * *

UNITED STATES PATENT AND TRADEMARK OFFICE
CERTIFICATE OF CORRECTION

PATENT NO. : 6,387,914 B2
DATED : May 14, 2002
INVENTOR(S) : Pascal Druzgala and Peter G. Milner It is certified that error appears in the above-identified patent and that said Letters Patent is hereby corrected as shown below:

Column 6,
Line 60, "$C_{2-20}$" should read -- $C_{1-20}$ --.
Line 67, "by. for" should read -- by, for --.

Column 11,
Line 11, "cyclopentylmalonatc" should read -- cyclopentylmalonate --.
Line 12, "29I" should read -- 291 --.

Column 16,
Line 24, "24" should read -- : 24 --.
Line 53, "2-Thiohydantoin" should read -- 2-thiohydantoin --.
Line 65, "1-Carboxymethylthiourea" should read -- 1-Carboxymethylthiourea: --

Column 18,
Line 31, "5-isoamylihio barbituric" should read -- 5-isoamylthiobarbituric --.
Line 40, "Carbethocyniethyl" should read -- Carbethoxymethyl --.
Line 49, "IN" should read -- 1N --.
Lines 51-52, "thiobarb ituric" should read -- thiobarbituric --.
Line 64, "dimeethylamnide" should read -- dimethylamide --.
Lines 64-65, "dipropyl/thiobarbituric" should read -- dipropylthiobarbituric --.
Lines 66-67, "cyclopenty/thiobarbituric" should read
-- cyclopentylthiobarbituric --.

Column 19,
Line 13, "Salts" should read -- Salts: --

Column 21,
Line 37, "R6=H" should read -- $R_6$=H --.

UNITED STATES PATENT AND TRADEMARK OFFICE
CERTIFICATE OF CORRECTION

PATENT NO. : 6,387,914 B2
DATED : May 14, 2002
INVENTOR(S) : Pascal Druzgala and Peter G. Milner It is certified that error appears in the above-identified patent and that said Letters Patent is hereby corrected as shown below:

Column 28,
Line 13, "R6" should read -- $R_6$ --.

Signed and Sealed this

Nineteenth Day of November, 2002

Attest:

Attesting Officer

JAMES E. ROGAN
Director of the United States Patent and Trademark Office